(12) United States Patent
Weber (10) Patent No.: US 7,507,433 B2
(45) Date of Patent: Mar. 24, 2009

(54) METHOD OF COATING A MEDICAL DEVICE USING AN ELECTROWETTING PROCESS

(75) Inventor: Jan Weber, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 571 days.

(21) Appl. No.: 10/934,681

(22) Filed: Sep. 3, 2004

(65) Prior Publication Data

US 2006/0052744 A1  Mar. 9, 2006

(51) Int. Cl.
*B05D 3/14* (2006.01)
*B05D 1/04* (2006.01)
*H05C 1/00* (2006.01)

(52) U.S. Cl. .................. 427/2.1; 427/2.24; 427/458; 427/472; 427/473

(58) Field of Classification Search ................ 427/472, 427/473, 483, 2.1–2.24
See application file for complete search history.

(56) References Cited

U.S. PATENT DOCUMENTS

| | | | |
|---|---|---|---|
| 2,359,476 A | 10/1944 | Gravley | |
| 4,655,771 A | 4/1987 | Wallsten | |
| 4,954,126 A | 9/1990 | Wallsten | |
| 5,688,563 A | 11/1997 | Louks et al. | |
| 5,824,049 A | 10/1998 | Ragheb et al. | |
| 6,096,070 A | 8/2000 | Ragheb et al. | |
| 6,425,914 B1 | 7/2002 | Wallace et al. | |
| 6,652,581 B1 * | 11/2003 | Ding | 623/1.39 |
| 6,743,463 B2 * | 6/2004 | Weber et al. | 427/2.24 |
| 7,147,763 B2 * | 12/2006 | Elrod et al. | 204/547 |
| 2002/0160123 A1 | 10/2002 | Fortuyn et al. | |
| 2003/0227100 A1 | 12/2003 | Chandross et al. | |

OTHER PUBLICATIONS

Frieder Mugele and Stephan Herminghaus, "Electrostatic Stabilization Of Fluid Microstructures," Applied Physics Letters, vol. 81, No. 12, pp. 2303-2305 (Sep. 16, 2002).
Anke Klinger, Stephan Herminghaus, and Frieder Mugele, "Self-Excited Oscillatory Dynamics Of Capillary Bridges In Electric Fields," Applied Physics Letters, vol. 82, No. 23, pp. 4187-4189 (Jun. 9, 2003).
Hyejin Moon, Robin L. Garrell, and Chang-Jin "CJ" Kim, "Low Voltage Electrowetting-On-Dielectric," Journal of Applied Physics, vol. 92, No. 7, pp. 4080-4087 (Oct. 1, 2002).

* cited by examiner

*Primary Examiner*—William Phillip Fletcher, III
*Assistant Examiner*—Cachet I Sellman
(74) *Attorney, Agent, or Firm*—Kenyon & Kenyon LLP (57) ABSTRACT

A method for coating at least a portion of a medical device is provided. The medical device has an insulator layer overlying an electrode on the insulator layer. The method includes arranging a liquid agent on at least the portion of the medical device. The method further includes applying an electrostatic potential to the electrode and applying another electrostatic potential to the liquid agent. A medical appliance having a coating applied by a method is provided. A system is provided for applying a liquid coating to a medical device.

17 Claims, 4 Drawing Sheets

METHOD OF COATING A MEDICAL DEVICE USING AN ELECTROWETTING PROCESS

FIELD OF THE INVENTION

The present invention relates to coating methods. More particularly, the present invention relates to a system and method for coating a medical device using an electrowetting process.

BACKGROUND INFORMATION

Medical devices may be coated so that the surfaces of such devices have desired properties or effects. For example, it may be useful to coat medical devices to provide for the localized delivery of therapeutic agents to target locations within the body, such as to treat localized disease (e.g., heart disease) or occluded body lumens. Localized drug delivery may avoid some of the problems of systemic drug administration, which may be accompanied by unwanted effects on parts of the body that are not to be treated. Additionally, treatment of the afflicted part of the body may require a high concentration of therapeutic agent that may not be achievable by systemic administration.

Localized drug delivery may be achieved, for example, by coating balloon catheters, stents and the like with the therapeutic agent to be locally delivered. The coating on medical devices may provide for controlled release, which may include long-term or sustained release, of a bioactive material. Additional exemplary devices may include artificial heart-valves, filters, catheters, contact lenses, etc.

Aside from facilitating localized drug delivery, medical devices may be coated with materials to provide beneficial surface properties. For example, medical devices may be coated with radiopaque materials to allow for fluoroscopic visualization while placed in the body. It is also useful to coat certain devices to achieve enhanced biocompatibility and to improve surface properties such as lubriciousness. Additionally, medical devices may require a coating layer for purposes of wear protection, color, or change in surface electrical or heat conductivity.

Coatings have been applied to medical devices by processes such as dipping, spraying, vapor deposition, plasma polymerization, spin-coating and electrodeposition. Although these processes have been used to produce satisfactory coatings, they have numerous associated potential drawbacks. For example, it may be difficult to achieve coatings of uniform thicknesses, both on individual parts and on batches of parts. Further, many conventional processes require multiple coating steps or stages for the application of a second coating material, or may require drying between coating steps or after the final coating step.

The spray-coating method has been used because of its excellent features, e.g., good efficiency and control over the amount or thickness of coating. However, conventional spray-coating methods, which may be implemented with a device such as an airbrush, have drawbacks. For example, when a medical device has a structure such that a portion of the device obstructs sprayed droplets from reaching another portion of the device, then the coating becomes uneven. Specifically, when a spray-coating is employed to coat a stent having a tube-like structure with openings, such as stents described in U.S. Pat. Nos. 4,655,771 and 4,954,126 to Wallsten, the coating on the inner wall of the tube-like structure may tend to be thinner than that applied to the outer wall of the tube-like structure. Hence, conventional spraying methods may tend to produce coated stents with coatings that are not uniform. Furthermore, conventional spraying methods are inefficient. In particular, generally only 5% of the coating solution that is sprayed to coat the medical device is actually deposited on the surface of the medical device. The majority of the sprayed coating solution may therefore be wasted.

In the spin-dipping process, a medical device is coupled to a spinning device, and then, while rotating about a central axis, the medical device is dipped into a coating solution to achieve the desired coating. This process also suffers from many inefficiencies including the unevenness of the coated layer and a lack of control over the coated layer's thickness.

In addition to the spray coating and spin-dipping methods, the electrostatic deposition method has been suggested for coating medical devices. For example, U.S. Pat. Nos. 5,824,049 and 6,096,070 to Ragheb et al. mention the use of electrostatic deposition to coat a medical device with a bioactive material. In the conventional electrodeposition or electrostatic spraying method, a surface of the medical device is electrically grounded and a gas may be used to atomize the coating solution into droplets. The droplets are then electrically charged using, for example, corona discharge, i.e., the atomized droplets are electrically charged by passing through a corona field. Since the droplets are charged, when they are applied to the surface of the medical device, they are attracted to the surface since it is grounded.

One disadvantage of conventional electrostatic spraying is that it requires a complicated spraying apparatus. In addition, because conventional electrostatic systems use a gas to move the droplets from a source to a target, controlling the gas pressure is crucial for accurate coating. However, it is not easy to control the gas pressure so that the target surface is evenly and sufficiently coated without losing much of the coating solution.

Devices may be coated by a gas assisted spraying process. A polymer/drug combination may be dissolved in a solvent mixture. The solution may be sprayed onto the devices and a polymer/drug film may be formed when the solvents evaporate. The ability to apply thin coatings on products may be limited by the capabilities of a gas assisted spraying process. The coating may flow on the medical device prior to drying, thereby creating an uneven concentration of bioactive agent on the surface of the device. A gas assisted spraying process may have a high variability for thin coatings. Additionally, the surface tension of the coating fluid and the wettability of the substrate surface may result in an undesired distribution of the coating fluid over the surface of the device, and may create an unnecessarily thick coating.

There is, therefore, a need for a cost-effective method of coating devices that results in thin, uniform, defect-free coatings and uniform drug doses per unit device. Each of the references cited herein is incorporated by reference herein for background information.

SUMMARY

A method for coating at least a portion of a medical device is provided. The medical device has an insulator layer overlying an electrode on at least the portion of the medical device. The method includes arranging a liquid agent on the insulator layer. The method further includes applying an electrostatic potential to the electrode and applying another electrostatic potential to the liquid agent.

The electrostatic potential and the other electrostatic potential may have at least one of a different magnitude and a different charge. The applying of the electrostatic potential to the electrode and the applying of the other electrostatic potential to the liquid bioactive agent may be performed simultaneously.

The arranging of the liquid bioactive agent may be performed either simultaneously with, or immediately before, the applying of the electrostatic potential to the electrode and the applying of the other electrostatic potential to the liquid bioactive agent. The method may further include drying the liquid bioactive agent on the medical device. The drying of the liquid bioactive agent may be performed either simultaneously with, or immediately after, the applying of the electrostatic potential to the electrode and the applying of the other electrostatic potential to the liquid bioactive agent. The drying of the liquid bioactive agent may be performed by waiting a predetermined time period, heating the medical device, or flowing a gas over the medical device.

The insulator layer may be arranged over the electrode on at least the portion of the medical device by spraying a liquid polymer on the medical device. The liquid polymer may include expanded polytetrafluoroethylene. The liquid agent may include a polymer including Paclitaxel. The arranging of the liquid agent may include dipcoating the medical device in a bath of the liquid agent or applying the liquid agent to a surface of the insulator layer with a syringe. The other electrostatic potential may be applied to the liquid agent by the syringe.

The electrode may include a metallic section of the medical device. The medical device may include the electrode. The insulator layer may overly an entire surface of the medical device. The medical device may be a stent or a balloon catheter. The insulator layer may include a porous structure. The pores of the porous structure may have a diameter between about 1 nanometer and about 1 micrometer.

A medical appliance having a coating applied by a method is provided. The medical device includes an insulating layer on at least a portion of a surface of the medical device. The method includes arranging a liquid agent on a first side of the insulating layer and arranging an electrode adjacent to a second side of the insulating layer. The second side is opposite the first side. The method further includes applying an electrostatic potential to the liquid agent and applying a different electrostatic potential to the electrode. The different electrostatic potential is applied simultaneously with the application of the electrostatic potential.

A system is provided for applying a liquid coating to a medical device. The system includes an arrangement for holding the medical device and a nozzle adapted to disburse the liquid coating and adapted to provide an electrostatic potential to the liquid coating. The system further includes an electrode electrically coupled to a metallic portion of the medical device. The electrode is adapted to provide a further electrostatic potential to the medical device. The further electrostatic potential has at least one of a different magnitude and a different charge than the electrostatic potential. The system further includes a source of the liquid coating adapted to provide the liquid coating to the nozzle.

DETAILED DESCRIPTION

Electrowetting is a process in which electrostatic fields are used to generate an additional pressure $P_{el}$ which is directed along the outward surface normal of the fluid. In other words, instead of just having the Laplace pressure $P_l$ responsible for creating the usual shapes of droplets on a surface, one can add an additional pressure $P_{el}$ and change the shape of the fluid surface by changing the electrostatic field strength.

Figure 1:
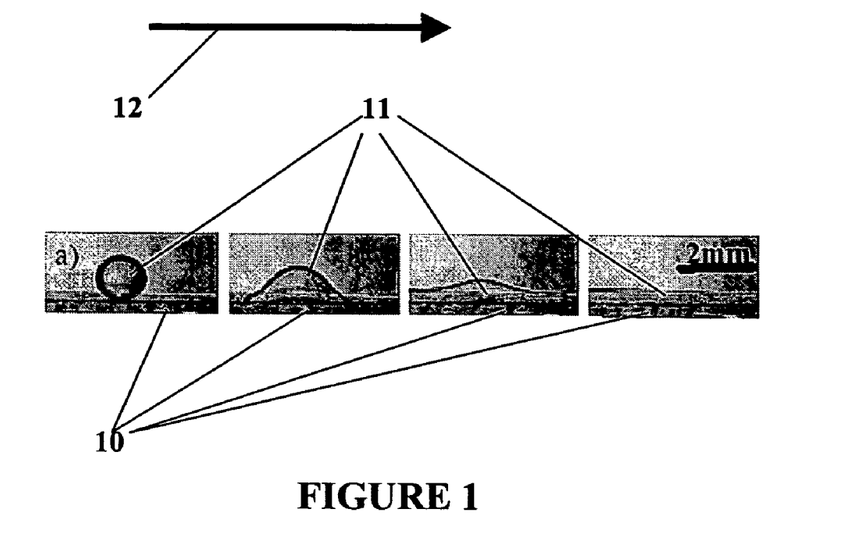
FIG. 1 shows a time-lapse photo series showing the electrowetting effect on a liquid drop on a surface.

FIG. 1 shows a time-lapse photo series showing the electrowetting effect on liquid drop 11 on insulator surface 10 subjected to an electrostatic field. As time progresses in the direction of arrow 12, an electrostatic potential is applied to an electrode below insulator surface 10 and a different electrostatic potential is applied to liquid drop 11. As the electric field is increased, liquid drop 11 spreads out over insulator surface 10. As is apparent, the contact angle between liquid drop 11 and insulator surface 10 decreases as the electrostatic field increases in the progression in the direction of arrow 12. Alternatively, time may be considered to progress in the direction opposite to arrow 12, in which case the electrostatic field is decreased over time.

Figure 2:
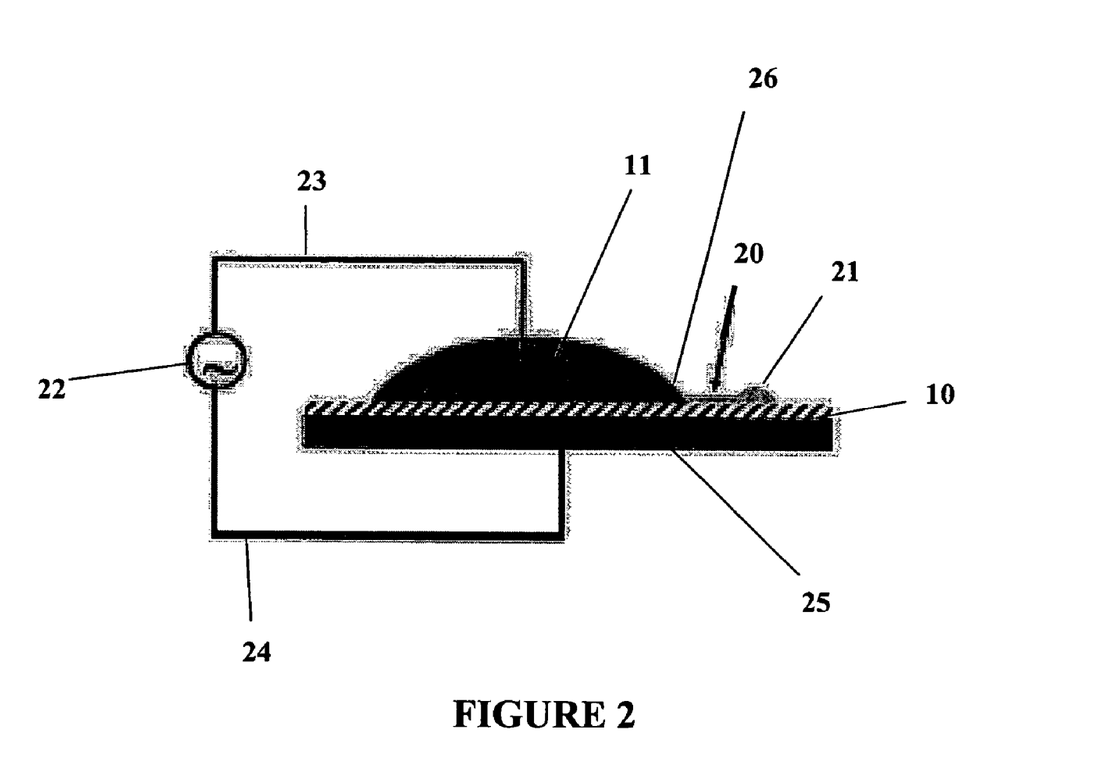
FIG. 2 is a schematic representation of a system for performing an exemplary method of the present invention.

FIG. 2 is a schematic representation of a system for performing an exemplary method of the present invention. Liquid drop 11 rests on top of insulator surface 10, which in turn rests on electrode surface 25. Voltage source 22 connects to electrode 23, which is in contact with liquid drop 11. Voltage source 22 may be a DC voltage source. Additionally, voltage source 22 connects to electrode 24, which is in contact with electrode surface 25. Application of an electrostatic potential (voltage) to electrodes 23 and 24, and by extension to liquid drop 11 and electrode surface 25, respectively, causes contact angle 26 to decrease and causes capillary bridge 20 to form, which allows fluid to flow from liquid drop 11 to satellite drop 21.

The substrate (insulator surface 10) may need to be non-conductive and the electric field may be arranged by connecting electrode 23 to the fluid of liquid drop 11 and electrode surface 25 underneath insulator surface 10, as shown in FIG. 2. The Lippmann equation expresses the relationship between an applied electric potential (V) and the resulting surface tension (γ) and is:

$$\gamma = \gamma_0 - (1/2)cV^2$$

Lippmann's equation may be expressed in term of the contact angle by incorporating Young's equation, which is:

$$\gamma_{SL} = \gamma_{SG} - \gamma_{LG} - \gamma \cos\theta$$

The resulting equation is called the Lippmann-Young equation and is:

$$\cos\theta = \cos\theta_0 + (1/\gamma_{LG})(1/2)cV^2$$

The contact angle of liquid drop 11 is given by the Lippmann-Young equation. In the example in FIG. 2, fluid is driven towards the small droplet (satellite drop 21) by applying a potential to the large droplet (liquid drop 11).

Not only is it possible to change the contact angle of fluids on a surface by using multiple electrodes, it is also possible to move droplets over a surface. For instance, a 6 nanoliter droplet (approximately 0.3 mm diameter) may be transferred at over 200 Hz on an electrode array.

Electrowetting technology may be used to improve the wettability of a surface. A metallic stent covered with a ceramic layer (e.g., TiOx) may be coated with a polymeric layer. Creating an electric contact with the metallic core of the stent at one point may enable utilization of the electrowetting technology since the ceramic layer acts as an insulator. The second electrode may be connected to a fluid bath allowing the stent to be dip-coated while the fluid spreads more easily over the stent. Use of the electrowetting technology may allow utilizing a higher viscosity coating material without the risk that coating bridges are created on the stent. One of the problems of utilizing a dip-coating process to coat a stent with a SIBS\Paclitaxel coating is that multiple dip-coatings steps are required to prevent clumping in and around the stent junctures and to prevent cracking of a thicker coating while drying. Use of the electrowetting technology to coat medical devices may enable a single dip-coat process for ceramic-coated stents. It is also possible to precoat a medical device with a thin polymer layer without drugs (for example a polyethylene oxide or a pure SIBS), after which one applies the electrowetting process to enable a one-step drug coating.

Figure 3:
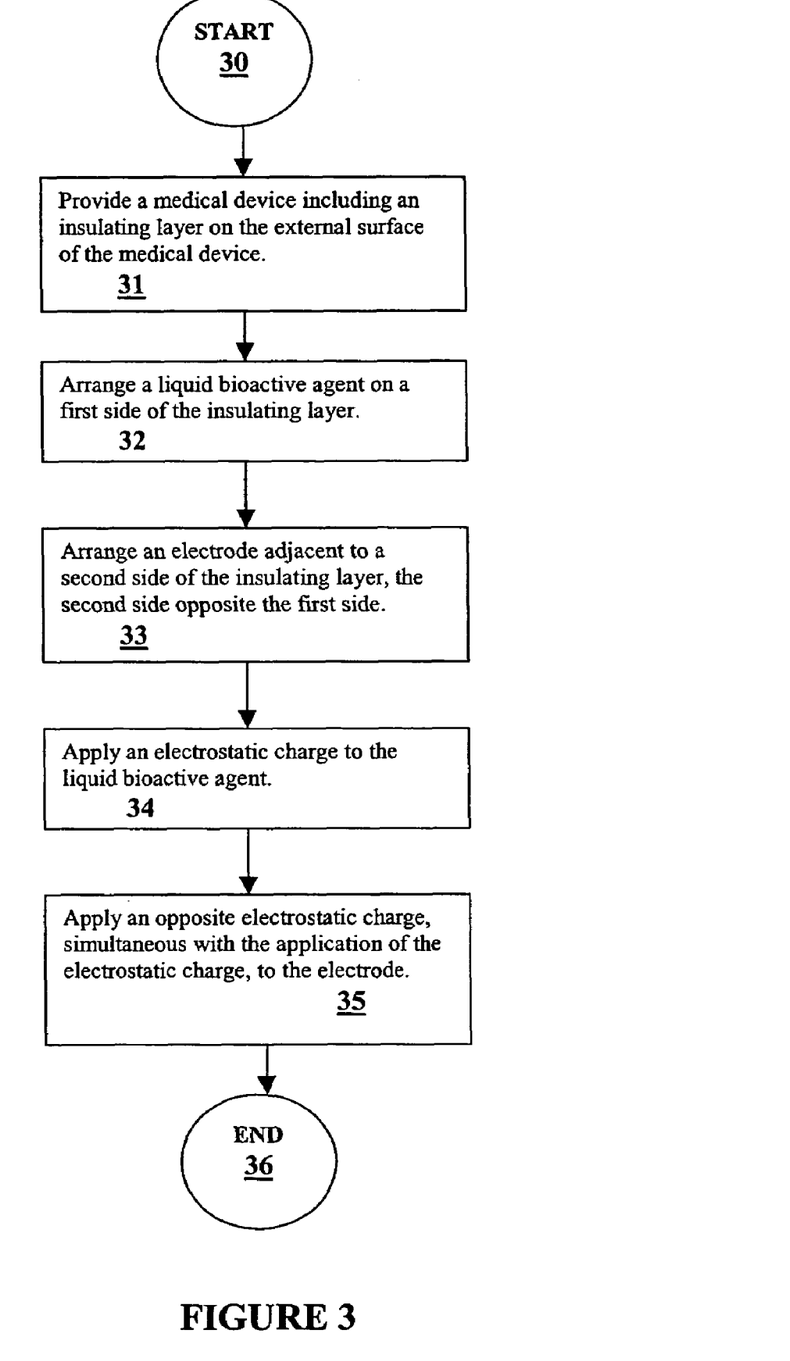
FIG. 3 is a flowchart for performing an exemplary method of the present invention.

FIG. 3 is a flowchart for performing an exemplary method of the present invention. The flow in FIG. 3 begins in start circle 30 and flows to action 31, which indicates to provide a medical device including an insulating layer on the external surface of the medical device. From action 31, the flow proceeds to action 32, which indicates to arrange a liquid bioactive agent on a first side of the insulating layer. From action 32, the flow proceeds to action 33, which indicates to arrange an electrode adjacent to a second side of the insulating layer, the second side opposite the first side. From action 33, the flow proceeds to action 34, which indicates to apply an electrostatic charge to the liquid bioactive agent. From action 34, the flow proceeds to action 35, which indicates to apply an opposite electrostatic charge, simultaneous with the application of the electrostatic charge, to the electrode. From action 35, the flow proceeds to end circle 36. The order of steps shown in FIG. 3 is not intended to be limiting. In particular, action 32 may be performed last, and drying steps may be performed subsequently. Additionally, some steps, for instance actions 34 and 35 may be performed simultaneously, and may be performed during the performance of other steps, for instance during action 32.

Figure 4:
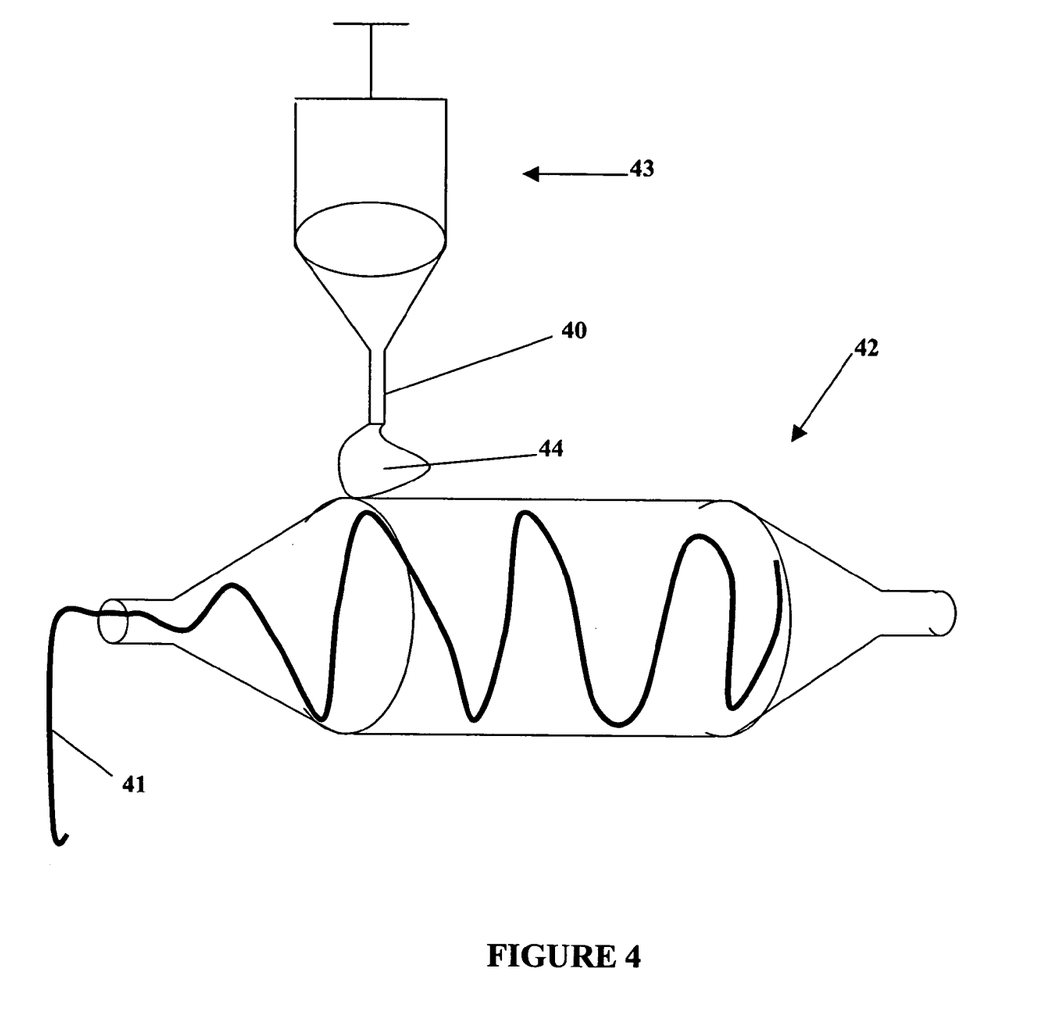
FIG. 4 is a schematic representation of an exemplary method according to the present invention used on a balloon catheter and using an electrode to form a pattern of material on the surface of the balloon catheter.

FIG. 4 is a schematic representation of an exemplary method according to the present invention used on balloon catheter 42 using electrode 41 to form a pattern of liquid material on the surface of balloon catheter 42. Electrode 41 is inserted into an interior space of balloon catheter 42 so that electrode 41 rests against or adjacent to an interior surface of balloon catheter 42. Balloon catheter 42 is composed partially or totally of an insulating material. Syringe 43 is used to deliver a liquid material to the external surface of balloon catheter 42. The liquid material is delivered from syringe 43 to nozzle 40, which also operates as an electrode. The liquid material may include a bioactive or therapeutic agent. Nozzle 40 delivers droplet 44 of liquid material to the surface of balloon catheter 42 with an electrostatic potential charged opposite to the charge of electrode 41. Due to the electrowetting effect of the opposite electrostatic potentials of nozzle 44 and electrode 41, which are separated by the insulating material of balloon catheter 42, the liquid material of droplet 44 will spread along the exterior surface of balloon catheter 42 following the pattern of electrode 41. This alternative exemplary embodiment of the present invention illustrates the use of a metallic syringe (or, alternatively, an inkjet nozzle) to deposit drops to the stent surface. The syringe (or, alternatively, the inkjet nozzle) may be used as a counter-electrode, instead of a fluidbath.

In an alternative exemplary embodiment of the present invention, an inner or outer surface of a catheter tube may be coated. To coat the inside of the tube, an electrode may be positioned to the outside of the tube and a fluid injected into the interior of the tube. Then a counter-electrode may be connected to the fluid column at one end of the tube.

In an alternative exemplary embodiment of the present invention, a coating may be spread across a highly hydrophobic surface (for example, ePTFE) used, for example, in filters.

For coating the interior of catheter tubes or the exterior of balloons, use of the electrowetting technology may allow the coating fluid to be restricted to defined areas. For instance, only at the location of the electric field is increased wettability obtained and the fluid is driven towards these locations. For example, a wire may be inserted into a balloon, as shown in FIG. 4. The wire may sit adjacent to one section of the balloon wall and form a pattern. Positioning a droplet of the coating fluid on the outside of the balloon at the location of the electrode will force the droplet to spread out along the pattern where the electrode wire is in contact with the inner surface of the balloon. As such, one can form spiral patterns or any other coating pattern on the balloon. Instead of connecting an electrode around a catheter tube in order to coat the entire inner lumen, one may also just place a spiral wire or other wire pattern on the outside. This will create a similar coating pattern within the lumen of the catheter tube.

Figure 5:
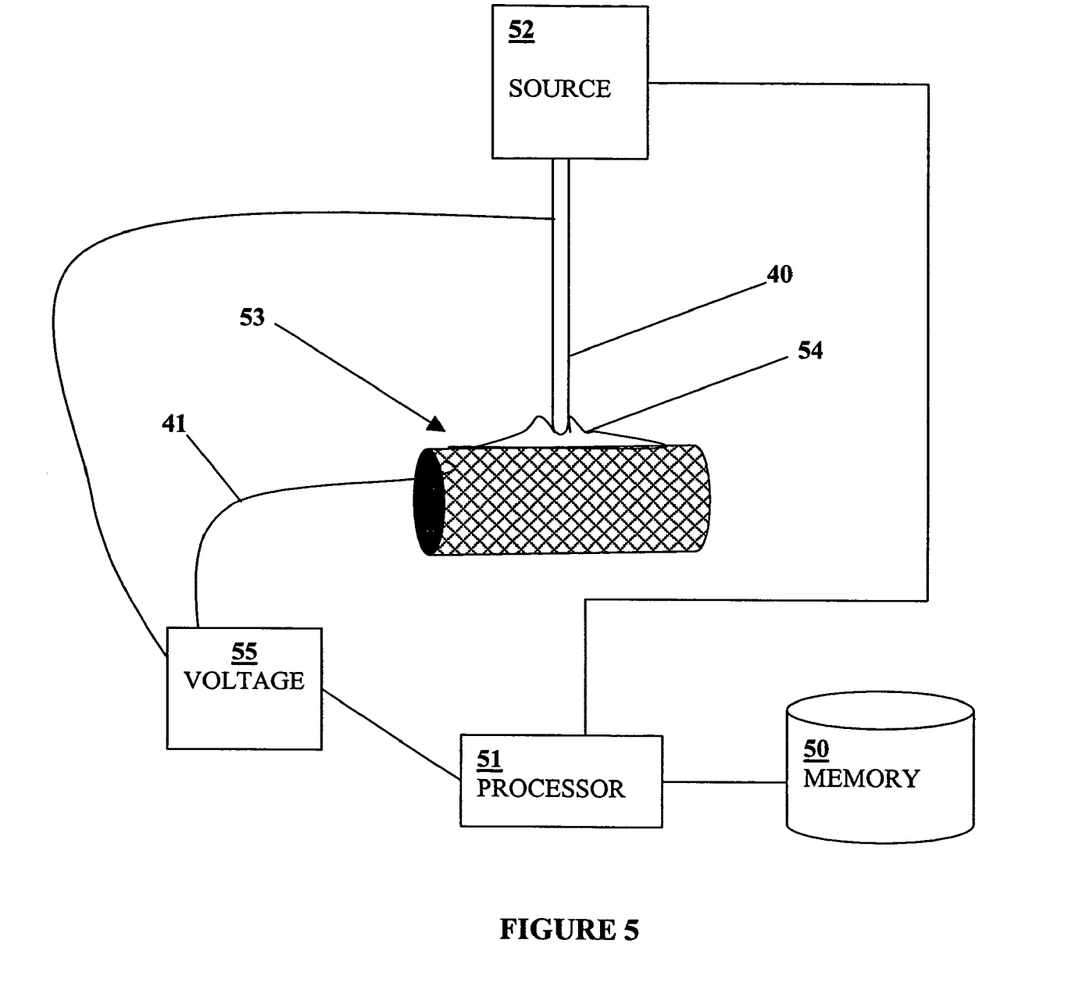
FIG. 5 is a schematic representation of an exemplary system for performing an exemplary method according to the present invention on a stent.

FIG. 5 is a schematic representation of an exemplary system for performing an exemplary method according to the present invention on stent 53. Processor 51 controls electrostatic potential source 55 (also referred to herein as a voltage source) that connects to electrode 41. Electrode 41 may electrically couple to a metallic core of stent 53. The metallic core of stent 53 may extend throughout stent 53 or only throughout a portion of stent 53. Additionally or alternatively, electrode 41 may rest against an interior surface of stent 53. In this situation, stent 53 may not have a metallic core. In any case, stent 53 may have an insulating material on at least a portion of an exterior surface. Additionally, electrode 41 may also serve a holding function, maintaining stent 53 in a stable position while stent 53 is being coated. Alternatively, stent 53 may be held by an arrangement for holding stents, for instance a cross-wire frame. Processor 51 also controls source 52 to deliver a bioactive material to nozzle 40. Alternatively, source 52 may deliver another type of coating to nozzle 40, for instance, a lubriciousness coating. Electrostatic potential source 55 is electrically coupled to nozzle 40 and processor 51 controls electrostatic potential source 55 to provide an electrostatic potential to nozzle 40 that is either oppositely charged and/or of a different magnitude than the electrostatic potential provided to electrode 41. Nozzle 40 therefore delivers the bioactive material (or other coating material) to the surface of stent 53 with an electrostatic charge in the form of liquid drop 54. Additionally, nozzle 40 may maintain contact with liquid drop 54 to promote the electrowetting effect by applying an electrostatic potential to liquid drop 54. An electrostatic field is caused by the difference between the electrostatic potential in liquid drop 54, which is electrically coupled to nozzle 40, and the electrostatic potential at electrode 41 (or a metallic core of stent 53 that is in contact with electrode 41). This electrostatic field causes liquid drop 54 (and the bioactive material therein) to form a thin coating wherever electrode 41 is situated under the external surface of stent 53. Processor 51 is coupled to memory 50, which may hold computer-readable instructions relating to the control of electrostatic potential source 55 and/or source 52.

Additionally, the electrowetting process may be used for filling porous ceramic or porous polymer structures. One of the problems with filling nano- or micro-porous structures with a drug is how to get the liquid containing the drug into the pores. Applying the electrowetting principle may assist in helping the fluid to pass into the pores.

As used herein, the term "bioactive agent" or "therapeutic agent" includes one or more "therapeutic agents" or "drugs". The terms "therapeutic agents", "active substance" and "drugs" are used interchangeably herein and include pharmaceutically active compounds, nucleic acids with and without carrier vectors such as lipids, compacting agents (such as histones), virus (such as adenovirus, adenoassociated virus, retrovirus, lentivirus and α-virus), polymers, hyaluronic acid, proteins, cells and the like, with or without targeting sequences.

The therapeutic agent may be any pharmaceutically acceptable agent such as a non-genetic therapeutic agent, a biomolecule, a small molecule, or cells.

Exemplary non-genetic therapeutic agents include antithrombogenic agents such heparin, heparin derivatives, prostaglandin (including micellar prostaglandin E1), urokinase, and PPack (dextrophenylalanine proline arginine chloromethylketone); anti-proliferative agents such as enoxaprin, angiopeptin, sirolimus (rapamycin), tacrolimus, everolimus, monoclonal antibodies capable of blocking smooth muscle cell proliferation, hirudin, and acetylsalicylic acid; anti-inflammatory agents such as dexamethasone, rosiglitazone, prednisolone, corticosterone, budesonide, estrogen, estradiol, sulfasalazine, acetylsalicylic acid, mycophenolic acid, and mesalamine; anti-neoplastic/anti-proliferative/anti-mitotic agents such as paclitaxel, epothilone, cladribine, 5-fluorouracil, methotrexate, doxorubicin, daunorubicin, cyclosporine, cisplatin, vinblastine, vincristine, epothilones, endostatin, trapidil, halofuginone, and angiostatin; anti-cancer agents such as antisense inhibitors of c-myc oncogene; anti-microbial agents such as triclosan, cephalosporins, aminoglycosides, nitrofurantoin, silver ions, compounds, or salts; biofilm synthesis inhibitors such as non-steroidal anti-inflammatory agents and chelating agents such as ethylenediaminetetraacetic acid, O,O'-bis(2-aminoethyl)ethylenenegly-col-N,N,N',N'-tetraacetic acid and mixtures thereof; antibiotics such as gentamycin, rifampin, minocyclin, and ciprofolxacin; antibodies including chimeric antibodies and antibody fragments; anesthetic agents such as lidocaine, bupivacaine, and ropivacaine; nitric oxide; nitric oxide (NO) donors such as linsidomine, molsidomine, L-arginine, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, warfarin sodium, Dicumarol, aspirin, prostaglandin inhibitors, platelet aggregation inhibitors such as cilostazol and tick antiplatelet factors; vascular cell growth promoters such as growth factors, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vascoactive mechanisms; inhibitors of heat shock proteins such as geldanamycin; and any combinations and prodrugs of the above.

Exemplary biomolecules include peptides, polypeptides and proteins; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Nucleic acids may be incorporated into delivery systems such as, for example, vectors (including viral vectors), plasmids or liposomes. Non-limiting examples of proteins include monocyte chemoattractant proteins ("MCP-1) and bone morphogenic proteins ("BMP's"), such as, for example, BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15. Preferred BMPS are any of BMP-2, BMP-3, BMP-4, BMP-5, BMP-6, and BMP-7. These BMPs can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them. Non-limiting examples of genes include survival genes that protect against cell death, such as anti-apoptotic Bcl-2 family factors and Akt kinase and combinations thereof. Non-limiting examples of angiogenic factors include acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor, and insulin like growth factor. A non-limiting example of a cell cycle inhibitor is a cathespin D (CD) inhibitor. Non-limiting examples of anti-restenosis agents include p15, p16, p18, p19, p21, p27, p53, p57, Rb, nFkB and E2F decoys, thymidine kinase ("TK") and combinations thereof and other agents useful for interfering with cell proliferation.

Exemplary small molecules include hormones, nucleotides, amino acids, sugars, and lipids and compounds have a molecular weight of less than 100 kD.

Exemplary cells include stem cells, progenitor cells, endothelial cells, adult cardiomyocytes, and smooth muscle cells. Cells can be of human origin (autologous or allogenic) or from an animal source (xenogenic), or genetically engineered. Non-limiting examples of cells include side population (SP) cells, lineage negative (Lin−) cells including Lin−CD34−, Lin−CD34+, Lin−cKit+, mesenchymal stem cells including mesenchymal stem cells with 5-aza, cord blood cells, cardiac or other tissue derived stem cells, whole bone marrow, bone marrow mononuclear cells, endothelial progenitor cells, skeletal myoblasts or satellite cells, muscle derived cells, go cells, endothelial cells, adult cardiomyocytes, fibroblasts, smooth muscle cells, adult cardiac fibroblasts+5-aza, genetically modified cells, tissue engineered grafts, MyoD scar fibroblasts, pacing cells, embryonic stem cell clones, embryonic stem cells, fetal or neonatal cells, immunologically masked cells, and teratoma-derived cells. Any of the therapeutic agents may be combined to the extent such combination is biologically compatible.

Any of the above-mentioned therapeutic agents may be incorporated into a polymeric coating on the medical device or applied onto a polymeric coating on a medical device. The polymers of the polymeric coatings may be biodegradable or non-biodegradable. Non-limiting examples of suitable non-biodegradable polymers include polystyrene; polyisobutylene copolymers and styrene-isobutylene-styrene block copolymers such as styrene-isobutylene-styrene tert-block copolymers (SIBS); polyvinylpyrrolidone including cross-linked polyvinylpyrrolidone; polyvinyl alcohols, copolymers of vinyl monomers such as EVA; polyvinyl ethers; polyvinyl aromatics; polyethylene oxides; polyesters including polyethylene terephthalate; polyamides; polyacrylamides; polyethers including polyether sulfone; polyalkylenes including polypropylene, polyethylene and high molecular weight polyethylene; polyurethanes; polycarbonates, silicones; siloxane polymers; cellulosic polymers such as cellulose acetate; polymer dispersions such as polyurethane dispersions (BAYHDROL®); squalene emulsions; and mixtures and copolymers of any of the foregoing.

Non-limiting examples of suitable biodegradable polymers include polycarboxylic acid, polyanhydrides including maleic anhydride polymers; polyorthoesters; poly-amino acids; polyethylene oxide; polyphosphazenes; polylactic acid, polyglycolic acid and copolymers and mixtures thereof such as poly(L-lactic acid) (PLLA), poly(D,L,-lactide), poly (lactic acid-co-glycolic acid), 50/50 (DL-lactide-co-glycolide); polydioxanone; polypropylene fumarate; polydepsipeptides; polycaprolactone and co-polymers and mixtures thereof such as poly(D,L-lactide-co-caprolactone) and polycaprolactone co-butylacrylate; polyhydroxybutyrate valerate and blends; polycarbonates such as tyrosine-derived polycarbonates and arylates, polyiminocarbonates, and polydimethyltrimethylcarbonates; cyanoacrylate; calcium phosphates; polyglycosaminoglycans; macromolecules such as polysaccharides (including hyaluronic acid; cellulose, and hydroxypropylmethyl cellulose; gelatin; starches; dextrans; alginates and derivatives thereof), proteins and polypeptides; and mixtures and copolymers of any of the foregoing. The biodegradable polymer may also be a surface erodable polymer such as polyhydroxybutyrate and its copolymers, polycaprolactone, polyanhydrides (both crystalline and amorphous), maleic anhydride copolymers, and zinc-calcium phosphate.

Such coatings used with the present invention may be formed by any method known to one in the art. For example, an initial polymer/solvent mixture can be formed and then the therapeutic agent added to the polymer/solvent mixture. Alternatively, the polymer, solvent, and therapeutic agent can be added simultaneously to form the mixture. The polymer/solvent mixture may be a dispersion, suspension or a solution. The therapeutic agent may also be mixed with the polymer in the absence of a solvent. The therapeutic agent may be dissolved in the polymer/solvent mixture or in the polymer to be in a true solution with the mixture or polymer, dispersed into fine or micronized particles in the mixture or polymer, suspended in the mixture or polymer based on its solubility profile, or combined with micelle-forming compounds such as surfactants or adsorbed onto small carrier particles to create a suspension in the mixture or polymer. The coating may comprise multiple polymers and/or multiple therapeutic agents.

The coating can be applied to the medical device by any known method in the art including dipping, spraying, rolling, brushing, electrostatic plating or spinning, vapor deposition, air spraying including atomized spray coating, and spray coating using an ultrasonic nozzle. The coating is typically from about 1 to about 50 microns thick. In the case of balloon catheters, the thickness is preferably from about 1 to about 10 microns, and more preferably from about 2 to about 5 microns. Very thin polymer coatings, such as about 0.2-0.3 microns and much thicker coatings, such as more than 10 microns, are also possible. It is also within the scope of the present invention to apply multiple layers of polymer coatings onto the medical device. Such multiple layers may contain the same or different therapeutic agents and/or the same or different polymers. Methods of choosing the type, thickness and other properties of the polymer and/or therapeutic agent to create different release kinetics are well known to one in the art.

The medical device may also contain a radio-opacifying agent within its structure to facilitate viewing the medical device during insertion and at any point while the device is implanted. Non-limiting examples of radio-opacifying agents are bismuth subcarbonate, bismuth oxychloride, bismuth trioxide, barium sulfate, tungsten, and mixtures thereof.

Non-limiting examples of medical devices according to the present invention include catheters, guide wires, balloons, filters (e.g., vena cava filters), stents, stent grafts, vascular grafts, intraluminal paving systems, implants and other devices used in connection with drug-loaded polymer coatings. Such medical devices may be implanted or otherwise utilized in body lumina and organs such as the coronary vasculature, esophagus, trachea, colon, biliary tract, urinary tract, prostate, brain, lung, liver, heart, skeletal muscle, kidney, bladder, intestines, stomach, pancreas, ovary, cartilage, eye, bone, and the like.

While the present invention has been described in connection with the foregoing representative embodiment, it should be readily apparent to those of ordinary skill in the art that the representative embodiment is exemplary in nature and is not to be construed as limiting the scope of protection for the invention as set forth in the appended claims.

What is claimed is:

1. A method for coating at least a portion of a medical device, the medical device having an insulator layer overlying an electrode on at least the portion of the medical device, comprising:
   arranging a liquid agent on the insulator layer, wherein the insulator layer prevents electric current flow between the liquid agent and the electrode; and
   applying a first electrostatic potential to the electrode and a second electrostatic potential to the liquid agent, wherein the first electrostatic potential and second electrostatic potential cause the liquid agent to flatten into a uniform coating.

2. The method of claim 1, wherein the first electrostatic potential and the second electrostatic potential have at least one of a different magnitude or a different charge.

3. The method of claim 1, wherein the applying of the first electrostatic potential to the electrode and the applying of the second electrostatic potential to the liquid agent are performed simultaneously.

4. The method of claim 3, wherein the arranging of the liquid agent is performed at least one of simultaneously with, or immediately before, the applying of the first electrostatic potential to the electrode or the applying of the second electrostatic potential to the liquid agent.

5. The method of claim 1, further comprising drying the liquid agent on the medical device.

6. The method of claim 5, wherein the drying of the liquid agent is performed at least one of simultaneously with, or immediately after, the applying of the first electrostatic potential to the electrode and the applying of the second electrostatic potential to the liquid agent.

7. The method of claim 5, wherein the drying of the liquid agent is performed by at least one of waiting a predetermined time period, heating the medical device, or flowing a gas over the medical device.

8. The method of claim 1, wherein the insulator layer is arranged over the electrode on at least the portion of the medical device by spraying a liquid polymer on the medical device.

9. The method of claim 8, wherein the liquid polymer comprises expanded polytetrafluoroethylene.

10. The method of claim 1, wherein the liquid agent comprises a polymer including Paclitaxel.

11. The method of claim 1, wherein the arranging of the liquid agent comprises at least one of:
   dipcoating the medical device in a bath of the liquid agent; or
   applying the liquid agent to a surface of the insulator layer with a syringe.

12. The method of claim 11, wherein the second electrostatic potential is applied to the liquid agent by the syringe.

13. The method of claim 1, wherein the electrode comprises a metallic section of the medical device.

14. The method of claim 1, wherein the insulator layer overlies an entire surface of the medical device.

15. The method of claim 1, wherein the medical device is one of a stent or a balloon catheter.

16. The method of claim 1, wherein the insulator layer comprises a porous structure.

17. The method of claim 16, wherein pores of the porous structure have a diameter between about 1 nanometer and about 1 micrometer.

* * * * *